United States Patent
Yang et al.

(10) Patent No.: US 11,778,372 B2
(45) Date of Patent: Oct. 3, 2023

(54) VOICE RECEPTION DEVICE

(71) Applicant: Merry Electronics Co., Ltd., Taichung (TW)

(72) Inventors: Chen Mao Yang, Taichung (TW); Cheng-Lung Chu, Taichung (TW); Ping Hung Chu, Taichung (TW)

(73) Assignee: Merry Electronics Co., Ltd., Taichung (TW)

( * ) Notice: Subject to any disclaimer, the term of this patent is extended or adjusted under 35 U.S.C. 154(b) by 0 days.

(21) Appl. No.: 17/858,998

(22) Filed: Jul. 7, 2022

(65) Prior Publication Data
US 2023/0027858 A1  Jan. 26, 2023

Related U.S. Application Data

(60) Provisional application No. 63/221,491, filed on Jul. 14, 2021.

(30) Foreign Application Priority Data

Jun. 27, 2022  (TW) .................................. 111123916

(51) Int. Cl.
| | |
|---|---|
| *H04R 1/46* | (2006.01) |
| *H04R 1/34* | (2006.01) |
| *H04R 1/00* | (2006.01) |
| *H04R 3/00* | (2006.01) |
| *H04R 1/28* | (2006.01) |
| *A61M 1/14* | (2006.01) |
| *H04R 1/04* | (2006.01) |

(52) U.S. Cl.
CPC ............... *H04R 1/46* (2013.01); *A61M 1/154* (2022.05); *H04R 1/00* (2013.01); *H04R 1/04* (2013.01); *H04R 1/2869* (2013.01); *H04R 1/342* (2013.01); *H04R 3/00* (2013.01); *A61M 2205/3334* (2013.01); *A61M 2205/3375* (2013.01)

(58) Field of Classification Search
CPC .. A61M 2205/3375; A61M 2205/3334; A61M 1/154; A61B 7/04; H04R 1/04; H04R 1/08; H04R 1/222; H04R 1/227; H04R 1/342; H04R 1/46
See application file for complete search history.

(56) References Cited

U.S. PATENT DOCUMENTS

2017/0281120 A1* 10/2017 Mulumudi ............... H04R 1/46
2018/0177484 A1*  6/2018 Habboushe .............. A61B 7/04

* cited by examiner

*Primary Examiner* — Kile O Blair
(74) *Attorney, Agent, or Firm* — JCIPRNET

(57) ABSTRACT

A voice reception device includes a casing and at least two voice reception units. The casing includes a peripheral side wall, a bottom wall, a containing space formed in an inside of the peripheral side wall and the bottom wall, and a first opening end located at an end of the containing space. The voice reception units are disposed in the containing space. Each of the voice reception units includes a main body, a diaphragm, and a voice guiding channel. The main body has a chamber, and an end of the chamber has a second opening end. The diaphragm is connected to the second opening end of the main body. The voice guiding channel includes an importing end acoustically connected to the chamber and an exporting end opposite to the importing end and acoustically connected to a microphone.

10 Claims, 8 Drawing Sheets

VOICE RECEPTION DEVICE

CROSS-REFERENCE TO RELATED APPLICATION

This application claims the priority benefit of U.S. provisional application Ser. No. 63/221,491, filed on Jul. 14, 2021 and Taiwan application serial no. 111123916, filed on Jun. 27, 2022. The entirety of the above-mentioned patent applications are hereby incorporated by reference herein and made a part of this specification.

BACKGROUND

Technical Field

The disclosure relates to a voice reception device, and in particular relates to a voice reception device for attaching to a surface of a human skin.

Description of Related Art

Stethoscopes are often used in medicine to detect the physiological sounds of the human body. For example, when dialysis patients are undergoing dialysis, it is necessary to detect the sound of blood flow at the input end and the output end of the blood on the skin surface, so as to determine whether the dialysis operation is being performed normally. However, the physiological sounds detected by the stethoscope often contain noises such as ambient sounds and non-target physiological sounds, which interfere with the diagnosis. Therefore, how to preliminarily separate target physiological sounds and noise is an important issue in the development of stethoscope functions.

SUMMARY

The disclosure provides a voice reception device, which may improve the voice reception effect of the target audio.

The voice reception device of the disclosure includes a casing and at least two voice reception units. The casing includes a peripheral side wall, a bottom wall, a containing space formed in an inside of the peripheral side wall and the bottom wall, and a first opening end located at an end of the containing space. The at least two voice reception units are disposed in the containing space of the casing, and the at least two voice reception units are in a relationship of a laterally spaced arrangement. Each of the at least two voice reception units includes a main body, a diaphragm, and a voice guiding channel. The main body has a chamber, and an end of the chamber has a second opening end. The diaphragm is connected to the second opening end of the main body, a surface of the diaphragm is attached to a surface of a human skin, and another surface faces the chamber of the main body. The voice guiding channel includes an importing end and an exporting end opposite to the importing end, the importing end of the voice guiding channel is acoustically connected to the chamber, and the exporting end of the voice guiding channel is acoustically connected to a microphone.

In an embodiment of the disclosure, the voice guiding channel is disposed between the main body and the bottom wall of the casing.

In an embodiment of the disclosure, the voice guiding channel is formed in the main body.

In an embodiment of the disclosure, the exporting end of the voice guiding channel is located on a surface of the main body, and the microphone is attached to the surface and aligned with the exporting end of the voice guiding channel.

In an embodiment of the disclosure, the voice guiding channel is in a helical shape.

In an embodiment of the disclosure, the voice guiding channel is in a bent shape.

In an embodiment of the disclosure, the voice guiding channel has a predetermined length, so as to reduce a resonance point of the voice guiding channel and increase a signal strength in a frequency band of 500 Hz to 1 kHz.

In an embodiment of the disclosure, the voice reception device includes a circuit board, in which the circuit board is disposed in the casing and coupled to the microphone.

In an embodiment of the disclosure, each of the voice reception units includes an elastic member, and the elastic member is connected between the casing and the main body.

In an embodiment of the disclosure, the main body protrudes out of the casing through the first opening end, such that the diaphragm is located outside the casing.

Based on the above, in the voice reception device of the disclosure, a voice guiding channel is added between the diaphragm and the microphone. In this way, the length of the voice guiding channel may be determined according to the frequency band of the target audio, such that the target audio may resonate in the voice guiding channel and be enhanced, thereby improving the voice reception effect of the target audio and avoiding the interference caused by noise on the interpretation of the target audio.

DETAILED DESCRIPTION OF DISCLOSED EMBODIMENTS

Figure 1:
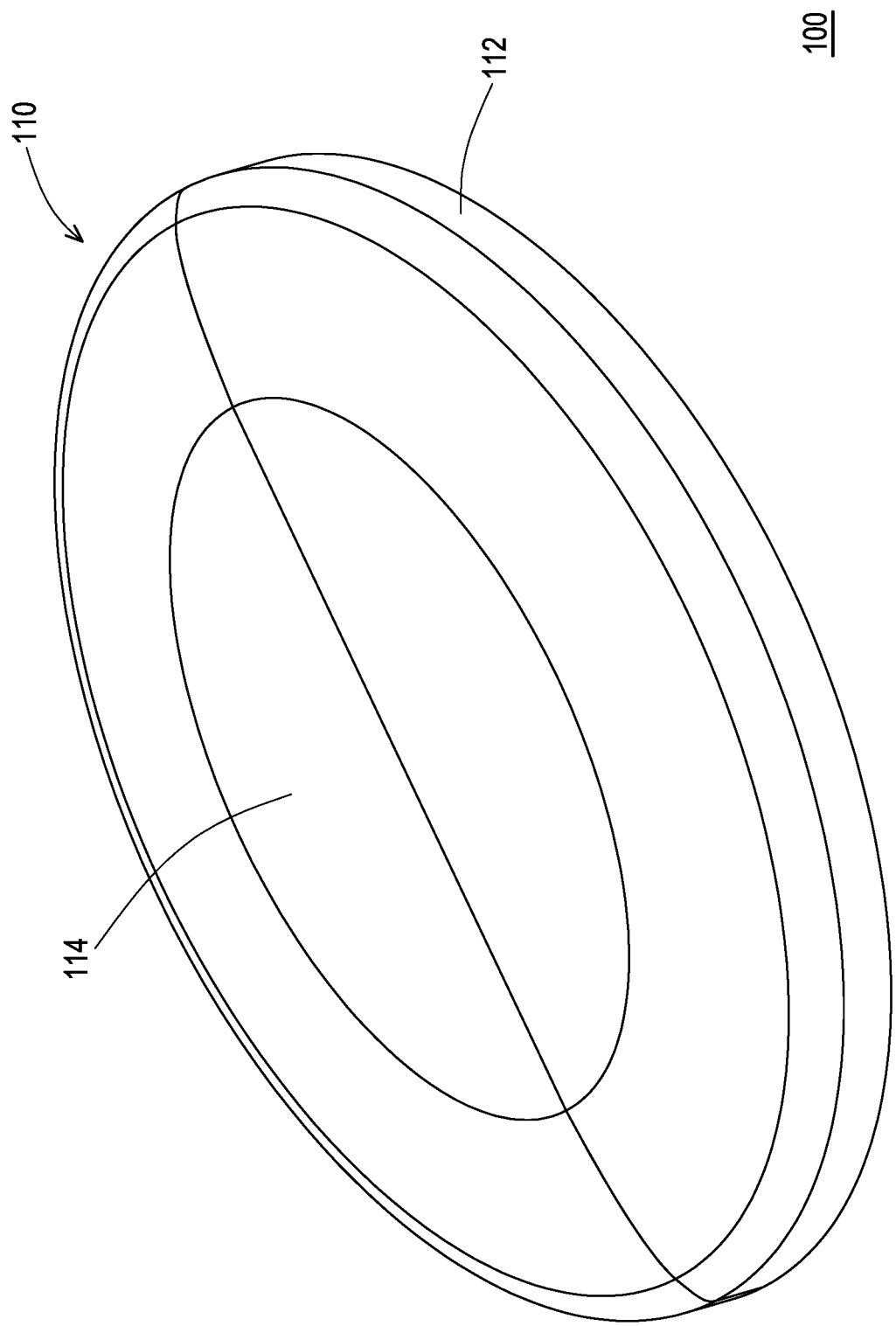
FIG. 1 is a three-dimensional view of a voice reception device according to an embodiment of the disclosure.
Figure 2:
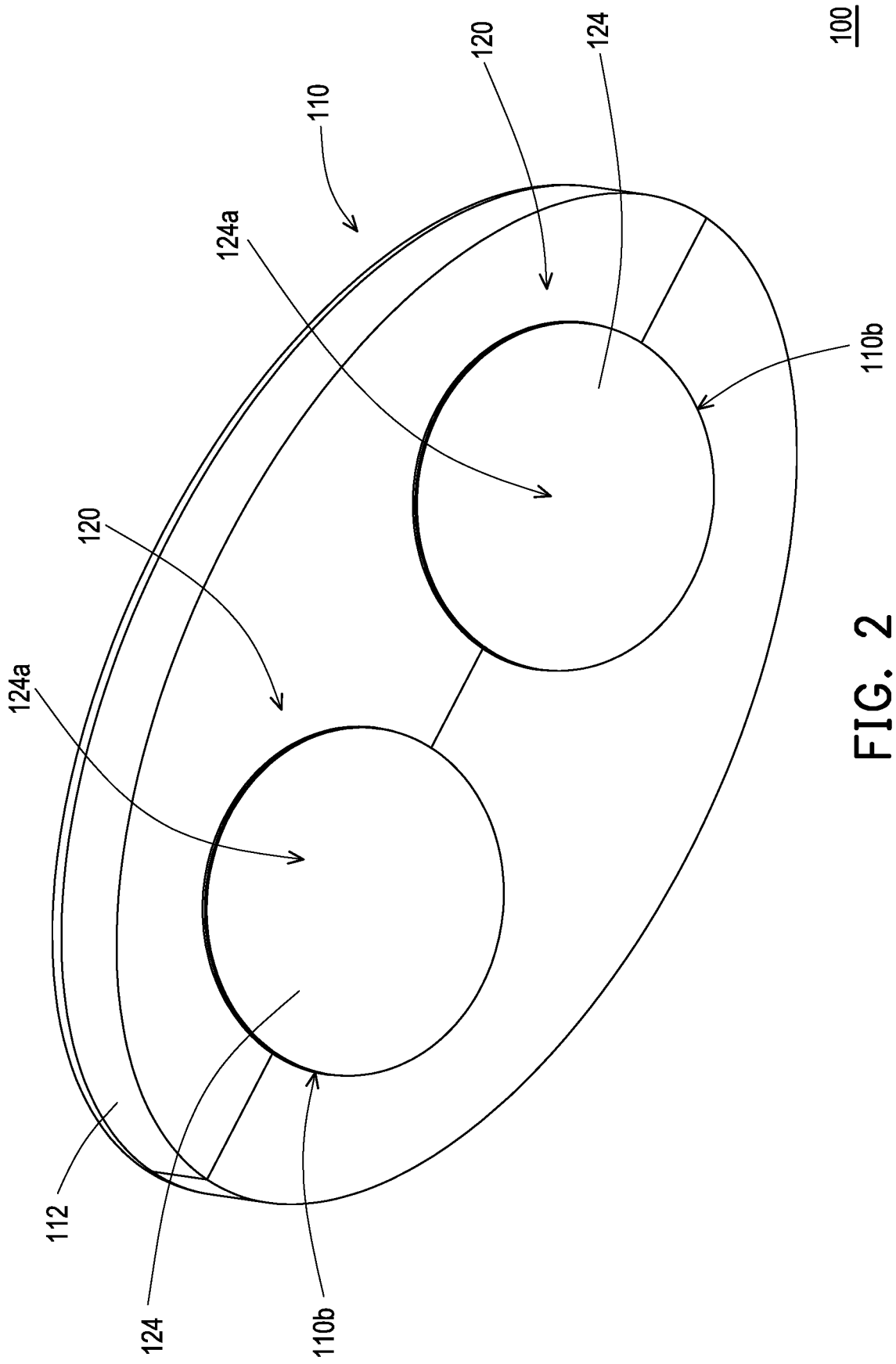
FIG. 2 is a three-dimensional view of the voice reception device of FIG. 1 from another viewing angle.
Figure 3:
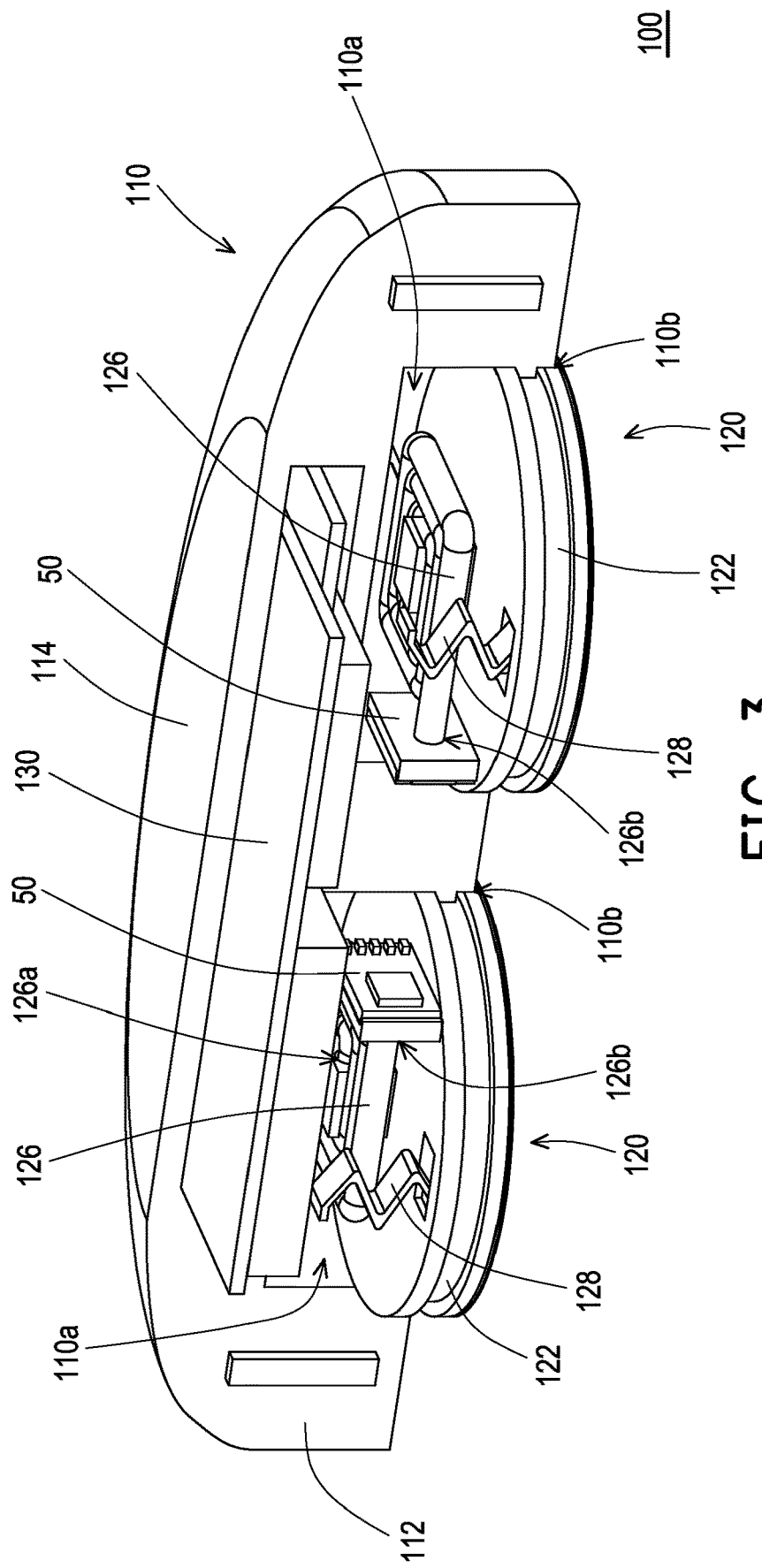
FIG. 3 is a three-dimensional view of a partial structure of the voice reception device of FIG. 1.

FIG. 1 is a three-dimensional view of a voice reception device according to an embodiment of the disclosure. FIG. 2 is a three-dimensional view of the voice reception device of FIG. 1 from another viewing angle. FIG. 3 is a three-dimensional view of a partial structure of the voice reception device of FIG. 1. Referring to FIG. 1 to FIG. 3, a voice reception device 100 of this embodiment includes a casing 110 and at least two voice reception units 120 (two are shown). The two voice reception units 120 are respectively connected to a microphone 50 for transmitting sound to the microphone 50 for voice reception. The voice reception device 100 of this embodiment is, for example, a medical stethoscope, and the two voice reception units 120 are, for example, used to respectively detect the sound of blood flow at the input end and the output end of the blood of the dialysis patient on the skin surface of the dialysis patient, so as to determine whether the dialysis operation is being performed normally. In other embodiments, the voice reception device 100 may be other types of devices, which are not limited in the disclosure.

Figure 4:
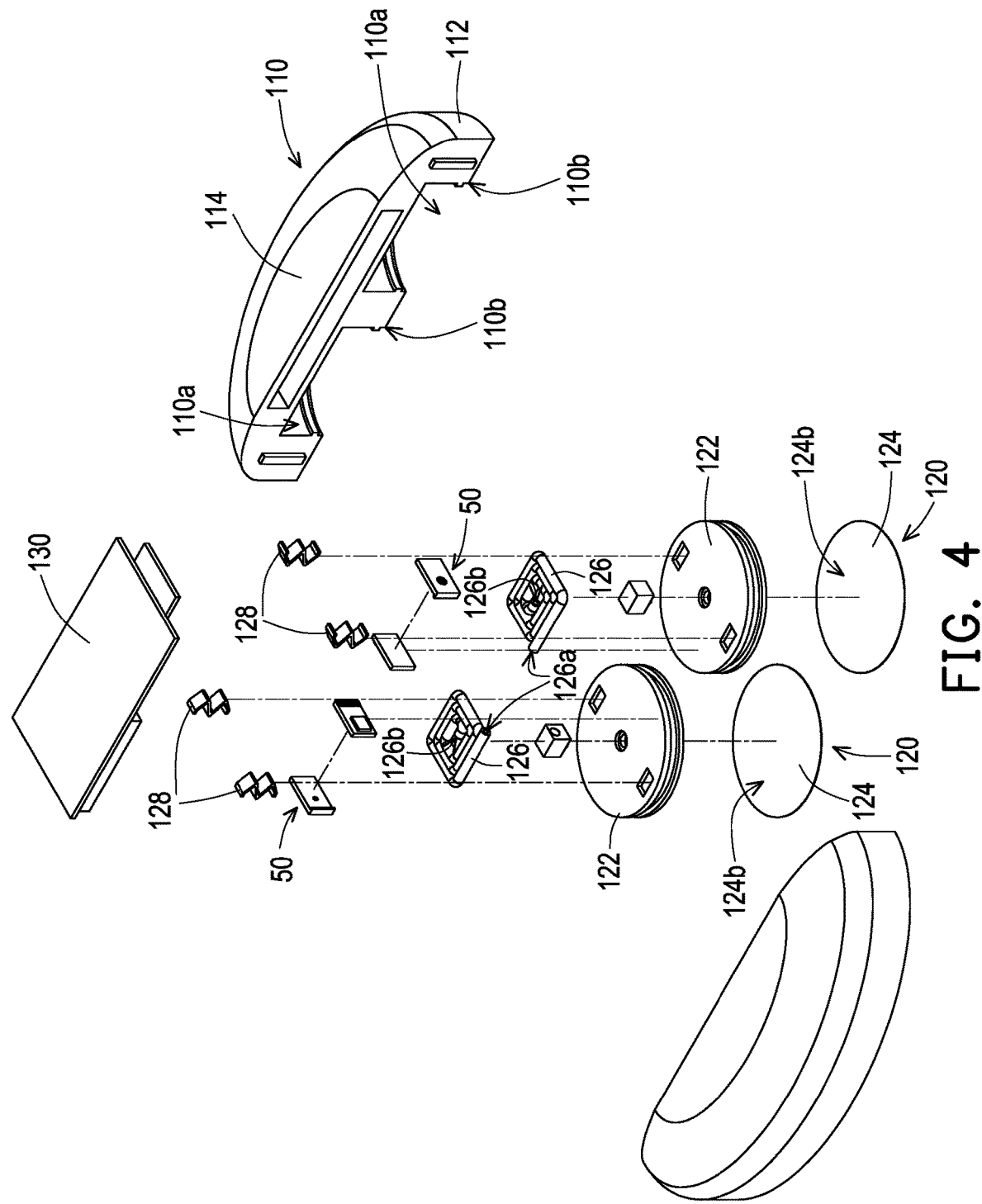
FIG. 4 is an exploded view of the voice reception device of FIG. 1.
Figure 5:
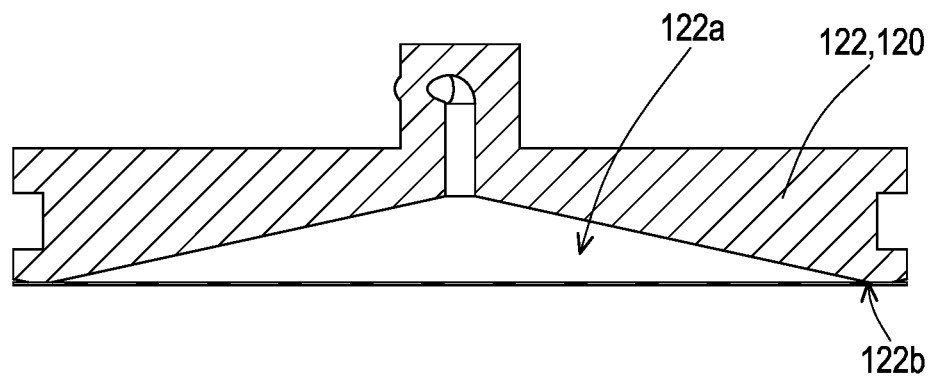
FIG. 5 is a cross-sectional view of the main body of FIG. 4.

FIG. 4 is an exploded view of the voice reception device of FIG. 1. FIG. 5 is a cross-sectional view of the main body of FIG. 4. Referring to FIG. 3 to FIG. 5, specifically, the casing 110 of this embodiment includes a peripheral side wall 112, a bottom wall 114, a containing space 110a (two are shown) formed in an inside of the peripheral side wall 112 and the bottom wall 114, and a first opening end 110b (two are shown) located at an end of the containing space 110a. The two voice reception units 120 are respectively disposed in the containing space 110a of the casing 110, and the two voice reception units 120 are in a relationship of a laterally spaced arrangement.

In more detail, each of the voice reception units 120 includes a main body 122, a diaphragm 124, and a voice guiding channel 126. The main body 122 has a chamber 122a, and an end of the chamber 122a has a second opening end 122b. The diaphragm 124 is connected to the second opening end 122b of the main body 122, a surface 124a of the diaphragm 124 is attached to a surface of a human skin, and another surface 124b of the diaphragm 124 faces the chamber 122a of the main body 122. The voice guiding channel 126 includes an importing end 126a and an exporting end 126b opposite to the importing end 126a. The importing end 126a of the voice guiding channel 126 is acoustically connected to the chamber 122a, and the exporting end 126b of the voice guiding channel 126 is acoustically connected to the microphone 50. The voice reception device 100 further includes a circuit board 130. The circuit board 130 is disposed in the casing 110 and coupled to the microphone 50. The sound waves generated by the vibration of the diaphragm 124 are transmitted to the microphone 50 through the voice guiding channel 126 for voice reception.

As described above, in the voice reception device 100 of this embodiment, a voice guiding channel 126 is added between the diaphragm 124 and the microphone 50. In this way, the length of the voice guiding channel 126 may be determined according to the frequency band of the target audio, such that the target audio may resonate in the voice guiding channel 126 and be enhanced, thereby improving the voice reception effect of the target audio and avoiding the interference caused by noise on the interpretation of the target audio. For example, if the frequency band of the target audio is 500 Hz to 1 kHz, the voice guiding channel 126 may be designed to have a predetermined length, so as to reduce the resonance point of the voice guiding channel 126 and increase the signal strength in the frequency band of 500 Hz to 1 kHz.

In this embodiment, the voice guiding channel 126 is disposed outside the main body 122 and between the main body 122 and the bottom wall 114 of the casing 110. In addition, the voice guiding channel 126 is, for example, in a bent shape so as to have a sufficient extension length (i.e., the above-mentioned predetermined length) in a limited arrangement space. In addition, the main body 122 of this embodiment protrudes out of the casing 110 through the first opening end 110b, such that the diaphragm 124 is located outside the casing 110 and may be attached to a target object (e.g., the surface of a human skin). Each of the voice reception units 120 in this embodiment further includes an elastic member 128. The elastic member 128 is connected between the casing 110 and the main body 122, such that the diaphragm 124 may closely contact the target object by the elastic force of the elastic member 128.

Figure 6:
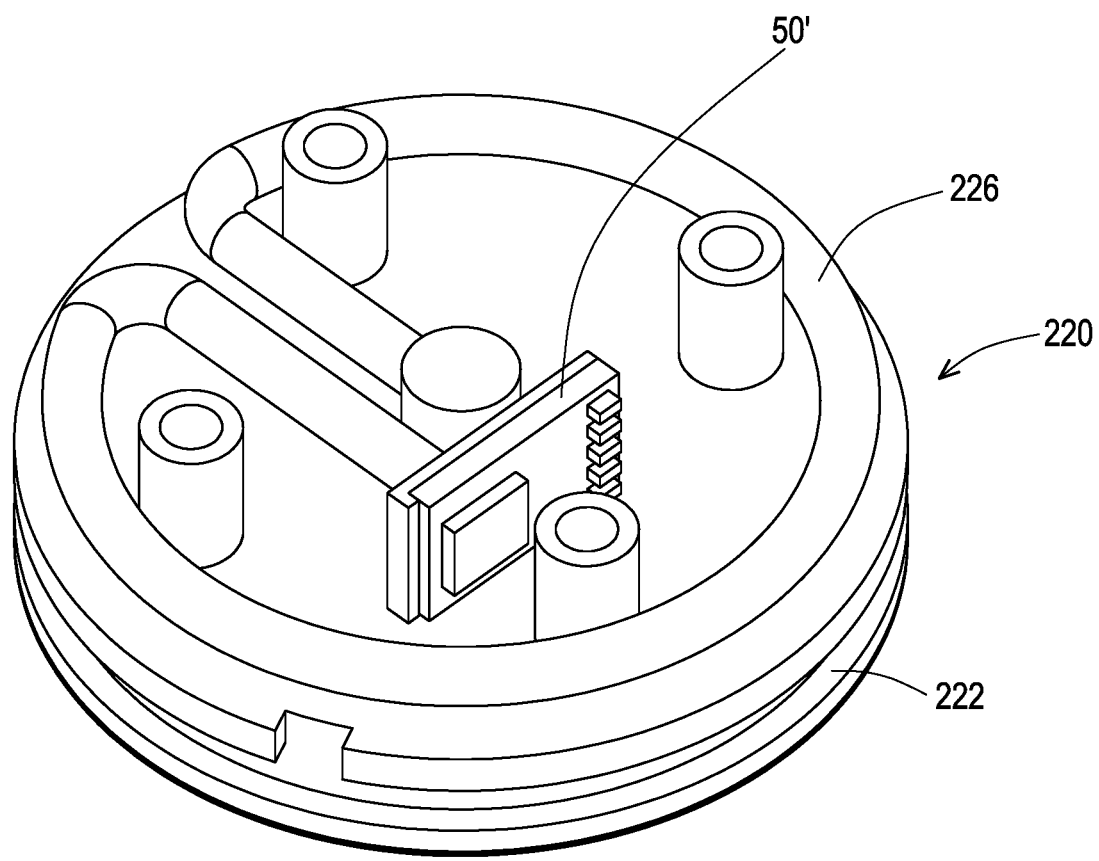
FIG. 6 is a three-dimensional view of some components of a microphone and a voice reception unit according to another embodiment of the disclosure.
Figure 7:
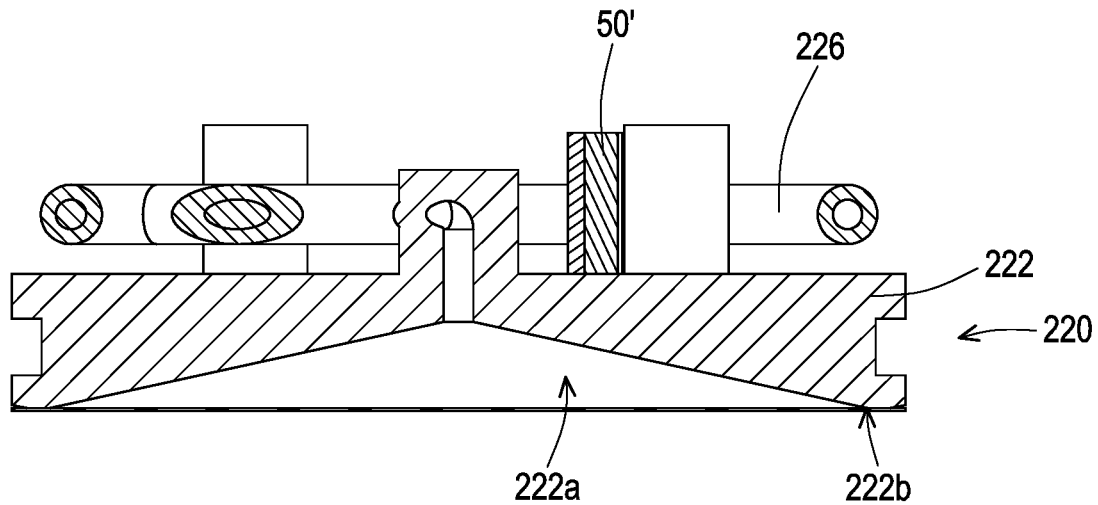
FIG. 7 is a cross-sectional view of some components of the microphone and the voice reception unit of FIG. 6.

FIG. 6 is a three-dimensional view of some components of a microphone and a voice reception unit according to another embodiment of the disclosure. FIG. 7 is a cross-sectional view of some components of the microphone and the voice reception unit of FIG. 6. In the voice reception unit 220 shown in FIG. 6 and FIG. 7, the configurations and functions of a main body 222, a chamber 222a, a second opening end 222b, a voice guiding channel 226, and a microphone 50' are the same or similar to the configurations and functions of the main body 122, the chamber 122a, the second opening end 122b, the voice guiding channel 126, and the microphone 50 of the forgoing embodiment, and are not repeated herein. The difference between the voice reception unit 220 shown in FIG. 6 and FIG. 7 and the voice reception unit 120 of the foregoing embodiment is that a portion of the voice guiding channel 226 of the voice reception unit 220 extends in an arc shape.

Figure 8:
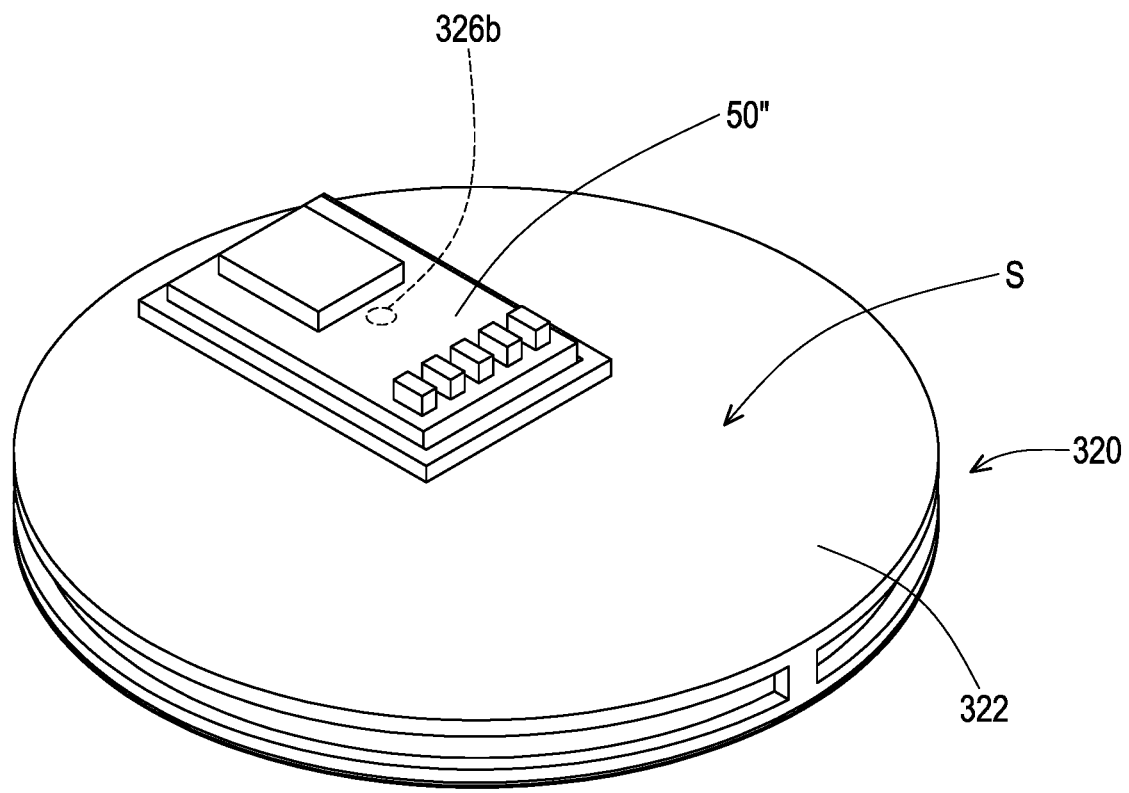
FIG. 8 is a three-dimensional view of some components of a microphone and a voice reception unit according to another embodiment of the disclosure.
Figure 9:
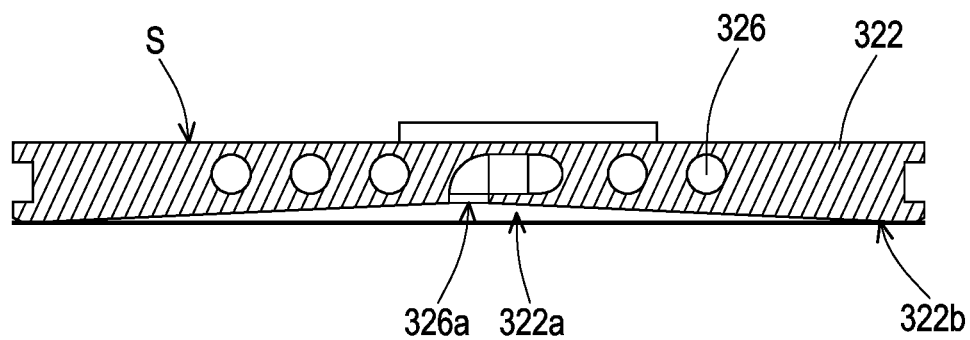
FIG. 9 is a cross-sectional view of some components of the voice reception unit of FIG. 8.
Figure 10:
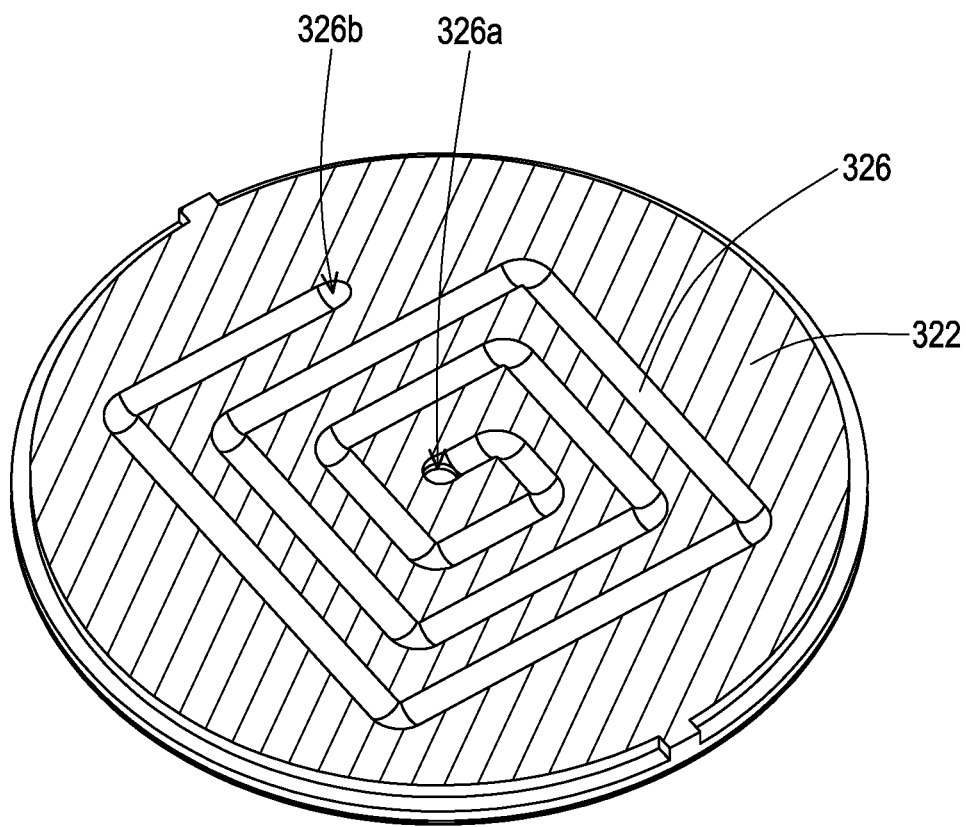
FIG. 10 is a three-dimensional view of a partial structure of the voice reception unit of FIG. 9.

FIG. 8 is a three-dimensional view of some components of a microphone and a voice reception unit according to another embodiment of the disclosure. FIG. 9 is a cross-sectional view of some components of the voice reception unit of FIG. 8. FIG. 10 is a three-dimensional view of a partial structure of the voice reception unit of FIG. 9. In a voice reception unit 320 shown in FIG. 8 to FIG. 10, the configurations and functions of a main body 322, a chamber 322a, a second opening end 322b, a voice guiding channel 326, an importing end 326a, an exporting end 326b, and a microphone 50" are the same or similar to the configurations and functions of the main body 122, the chamber 122a, the second opening end 122b, the voice guiding channel 126, the importing end 126a, the exporting end 126b, and the microphone 50 of the forgoing embodiment, and are not repeated herein. The difference between the voice reception unit 320 shown in FIG. 8 to FIG. 10 and the voice reception unit 120 of the foregoing embodiment is that the voice guiding channel 326 of the voice reception unit 320 is formed in the main body 322, the exporting end 326b of the voice guiding channel 326 is located on a surface S of the main body 322, and the microphone 50" is attached to the surface S and aligned with the exporting end 326b of the voice guiding channel 326. With this configuration, there is no need to additionally dispose a channel for forming the voice guiding channel 326 outside the main body 322, therefore the manufacturing cost may be lowered, and the overall thickness of the voice reception unit 320 may be reduced.

Figure 11:
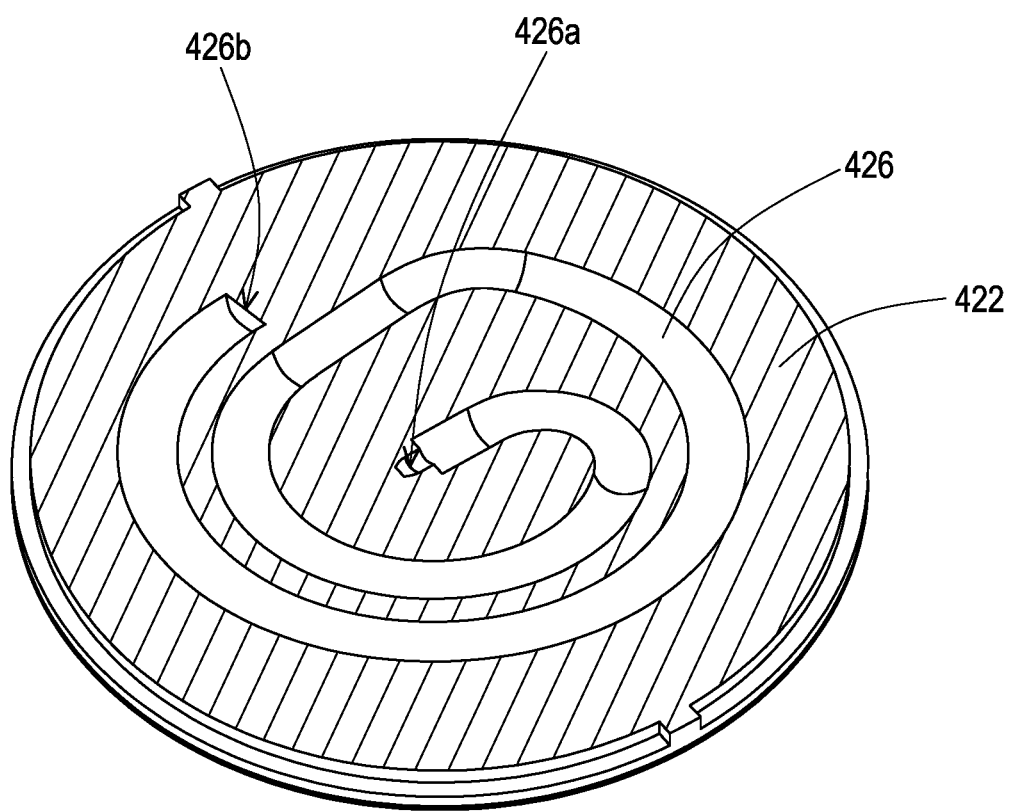
FIG. 11 is a three-dimensional view of a partial structure of a voice reception unit according to another embodiment of the disclosure.

FIG. 11 is a three-dimensional view of a partial structure of a voice reception unit according to another embodiment of the disclosure. The configurations and functions of a main body 422, a voice guiding channel 426, an importing end 426a, and an exporting end 426b shown in FIG. 11 are the same or similar to the configurations and functions of the main body 322, the voice guiding channel 326, the importing end 326a, and the exporting end 326b shown in FIG. 10, and are not repeated herein. The difference between the embodiment shown in FIG. 11 and the embodiment shown in FIG. 10 is that the voice guiding channel 426 is in a helical shape.

To sum up, in the voice reception device of the disclosure, a voice guiding channel is added between the diaphragm and the microphone. In this way, the length of the voice guiding channel may be determined according to the frequency band of the target audio, such that the target audio may resonate in the voice guiding channel and be enhanced, thereby improving the voice reception effect of the target audio and avoiding the interference caused by noise on the interpretation of the target audio. In addition, the voice guiding channel may be disposed outside the main body of the voice reception unit or formed in the main body of the voice reception unit according to design requirements, such that the design of the voice reception unit may be more flexible.

What is claimed is:

1. A voice reception device, comprising:
 a casing, comprising a peripheral side wall, a bottom wall, a containing space formed in an inside of the peripheral side wall and the bottom wall, and a first opening end located at an end of the containing space; and
 at least two voice reception units, disposed in the containing space of the casing, the at least two voice reception units being in a relationship of a laterally spaced arrangement, wherein each of the at least two voice reception units comprises:
  a main body, having a chamber, an end of the chamber having a second opening end;
  a diaphragm, connected to the second opening end of the main body, a surface of the diaphragm attaching to a surface of a human skin, another surface facing the chamber of the main body; and
  a voice guiding channel, comprising an importing end and an exporting end opposite to the importing end, wherein the importing end of the voice guiding channel is acoustically connected to the chamber, and the exporting end of the voice guiding channel is acoustically connected to a microphone.

2. The voice reception device according to claim 1, wherein the voice guiding channel is disposed between the main body and the bottom wall of the casing.

3. The voice reception device according to claim 1, wherein the voice guiding channel is formed in the main body.

4. The voice reception device according to claim 3, wherein the exporting end of the voice guiding channel is located on a surface of the main body, and the microphone is attached to the surface and aligned with the exporting end of the voice guiding channel.

5. The voice reception device according to claim 1, wherein the voice guiding channel is in a helical shape.

6. The voice reception device according to claim 1, wherein the voice guiding channel is in a bent shape.

7. The voice reception device according to claim 1, wherein the voice guiding channel has a predetermined length, so as to reduce a resonance point of the voice guiding channel and increase a signal strength in a frequency band of 500 Hz to 1 kHz.

8. The voice reception device according to claim 1, comprising a circuit board, wherein the circuit board is disposed in the casing and coupled to the microphone.

9. The voice reception device according to claim 1, wherein each of the at least two voice reception units comprises an elastic member, and the elastic member is connected between the casing and the main body.

10. The voice reception device according to claim 1, wherein the main body protrudes out of the casing through the first opening end, such that the diaphragm is located outside the casing.

* * * * *